United States Patent [19]
König et al.

[11] Patent Number: 5,922,886
[45] Date of Patent: Jul. 13, 1999

[54] PROCESS FOR PRODUCING N-SUBSTITUTED 3-HYDROXYPYRAZOLES

[75] Inventors: Hartmann König, Heidelberg; Norbert Götz, Worms; Ulrich Klein, Limburgerhof; Karsten Eller, Ludwigshafen, all of Germany

[73] Assignee: BASF Aktiengesellschaft, Ludwigshafen, Germany

[21] Appl. No.: 08/981,637

[22] PCT Filed: Jul. 2, 1996

[86] PCT No.: PCT/EP96/02891

§ 371 Date: Jan. 8, 1998

§ 102(e) Date: Jan. 8, 1998

[87] PCT Pub. No.: WO97/03969

PCT Pub. Date: Feb. 6, 1997

[30] Foreign Application Priority Data

Jul. 14, 1995 [DE] Germany .......................... 195 25 680

[51] Int. Cl.⁶ .................................................. C07D 231/10
[52] U.S. Cl. ....................................................... 548/374.1
[58] Field of Search ............................... 548/373.1, 374.1

[56] References Cited

PUBLICATIONS

J. of Chem. Soc. Perkin Trans. II, 1982, 1599–1603.
Acta Chem. Scand. 27 (1973) 2051–2074.
J. Fur Prakitische Chem., Band 313, Heft 1, 1971, S. 115–128.
J. Fur Praktische Chem., vol. 313(1), 1971, pp. 115–128.
J. Fur Praktische Chem. Band 313, Heft 2, 1971, S. 236–246.

*Primary Examiner*—Deborah C. Lambkin
*Assistant Examiner*—Ebenezer Sackey
*Attorney, Agent, or Firm*—Keil & Weinkauf

[57] ABSTRACT

N-substituted 3-hydroxypyrazoles of the formula I

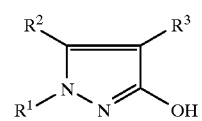

where $R^1$ is unsubstituted or substituted alkyl, aryl or heteroaryl and $R^2$, $R^3$ is hydrogen, cyano, halogen or unsubstituted or substituted alkyl, aryl or heteroaryl, are prepared by oxidation of a corresponding pyrazolidin-3-one with atmospheric oxygen in the presence of a metal salt in an essentially pH-neutral medium.

3 Claims, No Drawings

PROCESS FOR PRODUCING N-SUBSTITUTED 3-HYDROXYPYRAZOLES

This application is a 371 of PCT/EP96/02891 filed on Jul. 2, 1996 The present invention relates to a process for preparing N-substituted 3-hydroxypyrazoles of the formula I

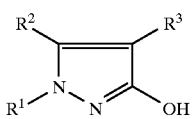

where
R$^1$ is unsubstituted or substituted alkyl, aryl or heteroaryl and
R$^2$, R$^3$ is hydrogen, cyano, halogen or unsubstituted or substituted alkyl, aryl or heteroaryl,
by oxidation of a pyrazolidin-3-one of the formula II

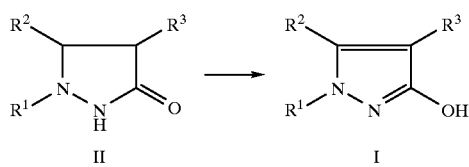

It is known from the literature that N-substituted 3-hydroxypyrazoles are obtained by oxidation of the corresponding pyrazolidinones [J. Gen. Chem. USSR, Engl. Trans. 31, 1770 (1961); Chem. Heterocycl. Comp. 5, 527 (1969); J. Prakt. Chem. 313, 115 (1971); J. Prakt. Chem. 318, 253 (1976); J. Med. Chem. 34, 1560 (1991); J. Prakt. Chem. 313, 1118 (1971); DE-A 34 15 385].

Oxidants used here are
elemental sulfur [J. Gen. Chem. USSR, Engl. Trans. 31, 1770 (1961)],
elemental halogens [Chem. Heterocycl. Comp. 5, 527 (1969); J. Prakt. Chem. 318, 253 (1976); J. Prakt. Chem. 313, 1118 (1971)],
peroxides [J. Med. Chem. 34, 1560 (1991); DE-A 34 15 385] and
atmospheric oxygen [J. Prakt. Chem. 313, 115 (1971); J. Prakt. Chem. 313, 1118 (1971)].

For the purposes of an industrial preparation of the 3-hydroxypyrazoles, the oxidation using elemental sulfur has the disadvantage that considerable amounts of reduction products of sulfur are formed and these require complicated work-up and disposal.

The use of elemental halogens is likewise not suitable for an industrial synthesis of the 3-hydroxypyrazoles, since the yields leave something to be desired. Furthermore, the use of large amounts of elemental halogen as oxidant is a drawback both for environmental reasons and also in view of the costs.

The known oxidation processes using peroxides require, on the one hand, complicated purifications and, on the other hand, use expensive reagents and give only unsatisfactory yields, so that they are not suitable for an industrial synthesis.

Only the use of atmospheric oxygen as oxidant offers a sensible alternative. However, the processes of this type which are known have the disadvantage that the reaction has to be carried out in a strongly acid medium. In the work-up, this gives rise to a considerable consumption of bases resulting in significant salt formation which is undesired from an ecological point of view. According to the literature, the oxidation by means of atmospheric oxygen is carried out in the presence of double molar amounts of iron salts or catalytic amounts of copper salts, with it being stated in the latter case that iron salts are inferior under catalytic conditions to the copper salts.

It is an object of the present invention to provide an economically and industrially safe and simple process for preparing 3-hydroxypyrazoles.

We have found that this object is achieved by a process for preparing N-substituted 3-hydroxypyrazoles of the formula I

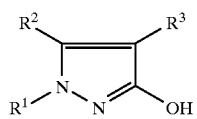

where
R$^1$ is unsubstituted or substituted alkyl, aryl or heteroaryl and
R$^2$, R$^3$ is hydrogen, cyano, halogen or unsubstituted or substituted alkyl, aryl or heteroaryl,
by oxidation of a pyrazolidin-3-one of the formula II

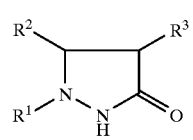

wherein the oxidation is carried out in the presence of metal salts using atmospheric oxygen as oxidant.

In the oxidation of the pyrazolidinones II, the procedure is generally to first admix an essentially neutral solution of II with catalytic amounts of a metal salt and subsequently to pass air into this mixture.

Suitable metal salts are, in particular, salts of iron in the oxidation state II or III (e.g. iron(II) chloride, iron(III) chloride, iron(II) sulfate and iron(III) sulfate), salts of copper in the oxidation state I or II (e.g. copper(I) chloride, copper(II) chloride, copper(I) sulfate and copper(II) sulfate) and also corresponding salts of main group or transition metals.

The metal salts are generally used in amounts of from 0.01 mol % to 20 mol %, preferably from 0.5 mol % to 10 mol %, in particular from 1 mol % to 5 mol %, based on IV [sic].

This oxidation is usually carried out at from 0° C. to the boiling point of the solvent used, preferably from 20° C. to 100° C.

Suitable solvents are water and aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, alcohols such as methanol, ethanol, n-propanol, iso-propanol, n-butanol and tert-butanol, carboxylic esters such as ethyl acetate and also N-methylpyrrolidone and dimethylformamide, particularly preferably dimethylformamide and N-methylpyrrolidone.

Mixtures of said solvents can also be used.

The reaction mixtures are worked up in a customary manner, e.g. by mixing with water, separating the phases and, if desired, purifying the crude products by chromatography. The intermediate and end products are sometimes obtained in the form of colorless or slightly brownish, viscous oils which are purified or freed of volatile constituents under reduced pressure and at moderately elevated temperature. If the intermediate and end products are obtained as solids, purification can also be carried out by recrystallization or digestion.

The 3-hydroxypyrazoles obtainable by the process of the present invention are suitable as intermediates for preparing dyes or active compounds in the pharmaceutical or crop protection sector.

Comparative examples:
1. Oxidation of pyrazolidinones using $FeCl_3$ [J. Prakt. Ch. 313, 1118 (1991)]

A solution of 23 g (0.142 mol) of $FeCl_3$ in 40 ml of $H_2O$ was added dropwise at room temperature to a mixture of 14 g (0.071 mol) of 1-(4-chlorophenyl)pyrazolidin-3-one and 100 ml of 1N HCl. After stirring overnight, 24 g of NaOH were added in portions, the mixture was heated to 90° C. and filtered with suction while hot. The precipitate was washed with boiling water.

After acidification of the filtrate to pH 5~6 and subsequent extraction with $CHCl_3$, a small amount of a dark residue was obtained from the organic phase. No product could be detected in this residue.

It was also not possible to isolate any product having sufficient purity for quantitative or qualitative characterization from the solid obtained from the aqueous phase and on filtration.

2. Oxidation of pyrazolidinones using $CUCl_2$ [J. prakt. Ch. 213, 115 (1971)]

2.1. Oxygen was passed for 8 hours at 50° C. into a mixture of 19.6 g (0.1 mol) of 1-(4-chlorophenyl)pyrazolidin-3-one, 200 ml of 1N HCl and 0.05 g of $CuCl_2·2 H_2O$ (0.293 mmol). The mixture was subsequently stirred overnight and the brown solid formed was filtered off with suction. This gave 17.7 g of a mixture of pyrazolinone and pyrazolidinone in a ratio of 4:1.

Calculated yield: 73%.

2.2. A similar experiment in which oxygen was passed in for 24 hours at 50° C. gave 17.8 g of a mixture whose spectroscopic and physical data were identical with those obtained under 2.1. The thin-layer chromatographic analysis carried out during the reaction showed that the amount of by-product steadily increased over the course of time. A further extension of the reaction time was therefore not examined.

Process examples according to the present invention:
1. Synthesis of 1-substituted pyrazolidin-3-ones
1.1. 1-(4-Chlorophenyl)pyrazolidin-3-one 90 g (0.9 mol) of ethyl acrylate are added dropwise at 40°–45° C. to a mixture of 15.9 g (234 mmol) of sodium ethoxide, 110 ml of ethanol, 110 ml of toluene and 25.7 g (180 mmol) of 4-chlorophenylhydrazine and the mixture is subsequently stirred for 1 hour at 40° C. The reaction mixture is evaporated to 100 ml and the residue is taken up in water. The resulting mixture is washed a number of times with toluene and the combined organic phases are extracted with 5% strength NaOH. The combined aqueous phases are adjusted to a pH of 6.5 and cooled to 10° C. The solid formed is filtered off with suction, washed with water and dried under reduced pressure.

Yield: 26.4 g (75% of theory) M.p.: 117°–120° C. (decomposition)

1.2. 1-(2,4-Dichlorophenyl)pyrazolidin-3-one 105.0 g (1.05 mol) of ethyl acrylate is added dropwise to a mixture of 37.3 g (211 mmol) of 2,4-dichlorophenylhydrazine, 18.6 g (273 mmol) of sodium ethoxide, 150 ml of ethanol and 150 ml of toluene and the mixture is subsequently stirred for 1 hour. The reaction mixture is evaporated to 100 ml and the residue is taken up in water. The organic phase is separated off and extracted with 5% strength NaOH. The combined aqueous phases are adjusted to a pH of 6.5 and the solid formed is filtered off with suction, washed with water and dried under reduced pressure.

Yield: 39.1 g (81% of theory) M.p.: 197°–199° C. (decomposition)

1.3. 1-(6-Chloro-2-pyridyl)pyrazolidin-3-one

A solution of 20.1 g (140 mmol) of 6-chloro-2-pyridylhydrazine (synthesis: Chem. Ber. 103. (1970) 1960) are added dropwise at 15°–20° C. to a mixture of 12.4 g (182 mmol) of sodium ethoxide, 100 ml of ethanol and 100 ml of toluene. After stirring for 2 hours at 25° C., the reaction mixture is evaporated, the residue is taken up in water and extracted with MTBE. The aqueous phase is adjusted to a pH of 6.5 and cooled to 5° C. The precipitate formed is filtered off and dried under reduced pressure at 40° C.

Yield: 21.6 g (78% of theory) M.p.: 116°–118° C. (decomposition)

2. Oxidation of pyrazolidinones using FeCl3
2.1. 1-(4-Chlorophenyl)-2H-pyrazolin-3-one 29.5 g (150 mmol) of 1-(4-chlorophenyl)pyrazolidin-3-one are dissolved in 100 ml of dimethylformamide and admixed with 2.4 g (15 mmol) of $FeCl_3$. While passing in air, the mixture is heated to 80° C., this temperature is held for 1 hour and the mixture is subsequently stirred for a further 12 hours without heating.

The reaction mixture is poured into 1 l of water, the precipitate formed is filtered off, washed with water and dried under reduced pressure.

Yield: 27.0 g (92% of theory) M.p.: 181°–182° C. (decomposition)

2.2. 1-(2,4-Dichlorophenyl)-2H-pyrazolin-3-one 39.0 g (169 mmol) of 1-(2,4-dichlorophenyl)pyrazolidin-3-one and 1.4 g (8.6 mmol) of $FeCl_3$ are dissolved in 220 ml of N-methylpyrrolidone, heated to 80° C. and air is passed through the reaction mixture for 18 hours. The mixture is subsequently poured into ice water. The solid formed is filtered off with suction, washed with water and dried under reduced pressure at 40° C.

Yield: 33.5 g (87% of theory) M.P.: 236°–237° C.

2.3. 1-(6-Chloro-2-pyridyl)-2H-pyrazolin-3-one 10.1 g (51 mmol) of 1-(6-chloro-2-pyridyl)pyrazolidin-3-one and 0.41 g (2.5 mmol) of $FeCl_3$ are dissolved in 50 ml of dimethylformamide. While passing in air, the mixture is first stirred for 1 hour at 25° C., then for 3 hours at 50° C. The reaction mixture is poured into 300 ml of ice water, the precipitate formed is filtered off, washed with water and dried under reduced pressure at 40° C.

Yield: 9.6 g (96% of theory) M.p.: 196°–199° C.

3. Oxidation of pyrazolidinones using CuCl
3.1. 1-(4-Chlorophenyl)-2H-pyrazolin-3-one Air is passed for 2 hours at 25° C. through a solution of 9.8 g (50 mmol) of 1-(4-chlorophenyl)pyrazolidin-3-one and 0.25 g (2.5 mmol) of CuCl in 50 ml of dimethylformamide. The reaction mixture is poured into water and stirred for 1 hour. The precipitate formed is filtered off, washed with water and dried under reduced pressure at 50° C. According to the m.p. and $^1$H NMR spectrum, the product is identical with that described under 2.1. Yield: 86% of theory.

3.2. 1-(2,4-Dichlorophenyl)-2H-pyrazolin-3-one 23.1 g (100 mmol) of 1-(2,4-dichlorophenyl)pyrazolidin-3-one and 0.5 g (5 mmol) of CuCl are dissolved in 230 ml of dimethylformamide, heated to 80° C. and air is passed through the reaction mixture for 9 hours. After stirring for 15 hours without heating and without passing in air, the mixture is heated while passing in air at 80° C. for 2 hours and at 100° C. for 2 hours. The reaction mixture is evaporated and the residue is stirred for 3 hours with 500 ml of $H_2O$. The solid is filtered off with suction, washed with n-hexane and with water and is dried under reduced pressure at 60° C. According to the m.p. and $^1H$ NMR spectrum, the product is identical with that described under 2.2. Yield: 85% of theory.

We claim:

1. A process for preparing N-substituted 3-hydroxypyrazoles of the formula I

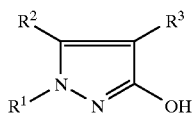

where $R^1$ is unsubstituted or substituted alkyl, aryl or heteroaryl and $R^2$, $R^3$ is hydrogen, cyano, halogen or unsubstituted or substituted alkyl, aryl or heteroaryl, by oxidation of a pyrazolidin-3-one of the formula II

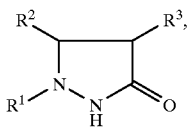

wherein the reaction is carried out in the presence of from 0.01 to 20 mol %, based on II, of metal salts using atmospheric oxygen as oxidant in an essentially pH-neutral medium.

2. A process as claimed in claim 1, wherein the metal salt used is an iron salt.

3. A process as claimed in claim 1, wherein the metal salt used is a copper salt.

* * * * *